US011364080B2

(12) United States Patent
Yildirim et al.

(10) Patent No.: US 11,364,080 B2
(45) Date of Patent: Jun. 21, 2022

(54) SYSTEM AND METHOD FOR PREDICTING TISSUE INTEGRITY

(71) Applicant: Howmedica Osteonics Corp., Mahwah, NJ (US)

(72) Inventors: Gokce Yildirim, Weehawken, NJ (US); John Parker, Pompton Lakes, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 184 days.

(21) Appl. No.: 16/778,058

(22) Filed: Jan. 31, 2020

(65) Prior Publication Data

US 2020/0163722 A1 May 28, 2020

Related U.S. Application Data

(62) Division of application No. 15/399,041, filed on Jan. 5, 2017, now Pat. No. 10,582,970.
(Continued)

(51) Int. Cl.
*A61B 34/10* (2016.01)
*G16H 50/20* (2018.01)
(Continued)

(52) U.S. Cl.
CPC .......... *A61B 34/10* (2016.02); *A61B 5/4509* (2013.01); *A61B 5/4533* (2013.01);
(Continued)

(58) Field of Classification Search
CPC ..... A61B 34/10; A61B 6/5217; A61B 5/4533; A61B 6/505; A61B 5/4509; A61B 5/7275;
(Continued)

(56) References Cited

U.S. PATENT DOCUMENTS 8,095,200 B2 1/2012 Quaid, III
2011/0184251 A1* 7/2011 Lo .................. G01N 33/5088
600/300
(Continued)

OTHER PUBLICATIONS

B.L. Van Meer, et al, "Bone mineral density changes in the knee following anterior cruciate ligament rupture"? Osteoarthritis and Cartilage., Jan. 2014, pp. 154-161, vol. 22, No. 1.
(Continued)

*Primary Examiner* — Rex R Holmes
(74) *Attorney, Agent, or Firm* — Lerner, David, Littenberg, Krumholz & Mentlik, LLP

(57) ABSTRACT

A system and method of diagnosing tissue integrity related to a joint of a patient may include imaging a first bone of the joint of the patient, determining a bone density profile of the first bone based on results of the imaging step, comparing the bone density profile of the first bone to at least one reference bone density profile of a reference first bone, and predicting an integrity of a tissue with respect to the first bone based on the comparison. The first bone may be a tibia and the bone density profile of the tibia may include a bone density profile of a sulcus of a medial tibial condyle of the tibia. The tissue may be an anterior cruciate ligament ("ACL") and the predicting step may include predicting the integrity of both an anteromedial bundle and a posterolateral bundle of the ACL.

12 Claims, 11 Drawing Sheets

Related U.S. Application Data

(60) Provisional application No. 62/275,432, filed on Jan. 6, 2016.

(51) Int. Cl.
| | | |
|---|---|---|
| *G16H 50/70* | (2018.01) | |
| *G16H 30/40* | (2018.01) | |
| *G16H 70/00* | (2018.01) | |
| *A61B 5/00* | (2006.01) | |
| *A61B 6/00* | (2006.01) | |
| *A61B 6/03* | (2006.01) | |

(52) U.S. Cl.
CPC ............ *A61B 5/7275* (2013.01); *A61B 6/505* (2013.01); *A61B 6/5217* (2013.01); *G16H 30/40* (2018.01); *G16H 50/20* (2018.01); *G16H 50/70* (2018.01); *G16H 70/00* (2018.01); *A61B 6/032* (2013.01); *A61B 2034/102* (2016.02); *A61B 2034/105* (2016.02); *A61B 2034/107* (2016.02)

(58) Field of Classification Search
CPC .............. A61B 6/032; A61B 2034/102; A61B 2034/105; A61B 2034/107; G16H 30/40; G16H 50/70; G16H 50/20
See application file for complete search history.

(56) References Cited

U.S. PATENT DOCUMENTS

| | | | |
|---|---|---|---|
| 2014/0180341 A1* | 6/2014 | Kang ................. | A61B 17/8095 606/281 |
| 2015/0080717 A1 | 3/2015 | Ferko | |
| 2015/0119987 A1 | 4/2015 | Davignon et al. | |
| 2017/0162078 A1* | 6/2017 | Imhauser ............... | G09B 23/30 |

OTHER PUBLICATIONS

Emovi, KneeKG Product Brochure, Innovative 3DKnee Function Assessment Device, 2012.
Extended European Search Report for Application No. 17150450.9 dated Apr. 21, 2017.
Seim, Heiko, et al. "Segmentation of bony structures with ligament attachment sites." Bildverarbeitung für die Medizin 2008. Springer, Berlin, Heidelberg, Apr. 2008, pp. 207-211.
Wing Hung Alex Ng, et al., "Imaging of the anterior cruciate ligament"?World Journal of Orthopedics, Jan. 2011 , p. 75, vol. 2, No. 8.
Wroble, R. R., et al., Repeatability of the KT-1000 arthrometer in a normal population, The American Journal of Sports Medicine, vol. 18, No. 4, 1990 American Orthopaedic Society for Sports Medicine.

\* cited by examiner

| Patient ID | Anterior Max | Posterior Max | Tubercle | | P/A ratio | T/A ratio | P/T ratio |
|---|---|---|---|---|---|---|---|
| 1 | 757 | 1126 | 722 | | 1.49 | 0.95 | 1.56 |
| 2 | 780 | 1212 | 730 | | 1.55 | 0.94 | 1.66 |
| 3 | 908 | 1500 | 1341 | | 1.65 | 1.48 | 1.12 |
| 4 | 1064 | 1328 | 1136 | | 1.25 | 1.07 | 1.17 |
| 5 | 953 | 1340 | 909 | | 1.41 | 0.95 | 1.47 |
| 6 | 711 | 993 | 960 | | 1.40 | 1.35 | 1.03 |
| 7 | 1063 | 1132 | 1254 | | 1.06 | 1.18 | 0.90 |
| 8 | 903 | 1189 | 1228 | | 1.32 | 1.36 | 0.97 |
| 9 | 1006 | 1191 | 868 | | 1.18 | 0.86 | 1.37 |
| 10 | 538 | 1210 | 625 | | 2.25 | 1.16 | 1.94 |
| 11 | 692 | 1329 | 625 | | 1.92 | 0.90 | 2.13 |
| 12 | 830 | 1273 | 944 | | 1.53 | 1.14 | 1.35 |
| 13 | 527 | 993 | 625 | | 1.88 | 1.19 | 1.59 |
| 14 | 1280 | 1384 | 1277 | | 1.08 | 1.00 | 1.08 |
| 15 | 978 | 1245 | 1100 | | 1.27 | 1.12 | 1.13 |
| 16 | 824 | 1160 | 971 | | 1.41 | 1.18 | 1.19 |
| 17 | 1054 | 1271 | 842 | | 1.21 | 0.80 | 1.51 |
| 18 | 717 | 1275 | 1016 | | 1.78 | 1.42 | 1.25 |
| 19 | 1095 | 1014 | 873 | | 0.93 | 0.80 | 1.16 |
| 20 | 304 | 908 | 345 | | 2.99 | 1.13 | 2.63 |
| | | | | Average | 1.53 | 1.02 | 1.49 |
| | | | | SD | 0.52 | 0.14 | 0.44 |
| | | | High Ratio | Average | 1.54 | 1.40 | 1.09 |
| | | | | SD | 0.22 | 0.06 | 0.12 |

*FIG. 8*

| Patient ID | Anterior Max | Posterior Max | Tubercle | | P/A ratio | T/A ratio | P/T ratio |
|---|---|---|---|---|---|---|---|
| 21 | 882 | 1047 | 869 | | 1.19 | 0.99 | 1.20 |
| 22 | 897 | 1264 | 1203 | | 1.41 | 1.34 | 1.05 |
| 23 | 941 | 1055 | 1097 | | 1.12 | 1.17 | 0.96 |
| 24 | 819 | 1227 | 1072 | | 1.50 | 1.31 | 1.14 |
| 25 | 899 | 1104 | 733 | | 1.23 | 0.82 | 1.51 |
| 26 | 934 | 1322 | 916 | | 1.42 | 0.98 | 1.44 |
| 27 | 927 | 1147 | 858 | | 1.24 | 0.93 | 1.34 |
| 28 | 1098 | 1482 | 1077 | | 1.35 | 0.98 | 1.38 |
| 29 | 887 | 997 | 923 | | 1.12 | 1.04 | 1.08 |
| 30 | 933 | 950 | 1073 | | 1.02 | 1.15 | 0.89 |
| 31 | 997 | 1155 | 1155 | | 1.16 | 1.16 | 1.00 |
| 32 | 821 | 947 | 969 | | 1.15 | 1.18 | 0.98 |
| 33 | 1413 | 1201 | 1406 | | 0.85 | 1.00 | 0.85 |
| 34 | 684 | 1053 | 570 | | 1.54 | 0.83 | 1.85 |
| 35 | 655 | 1112 | 823 | | 1.70 | 1.26 | 1.35 |
| 36 | 844 | 1358 | 1055 | | 1.61 | 1.25 | 1.29 |
| 37 | 826 | 1003 | 1133 | | 1.21 | 1.37 | 0.89 |
| 38 | 711 | 752 | 737 | | 1.06 | 1.04 | 1.02 |
| 39 | 574 | 862 | 620 | | 1.50 | 1.08 | 1.39 |
| 40 | 578 | 781 | 625 | | 1.35 | 1.08 | 1.25 |
| 41 | 794 | 896 | 1069 | | 1.12 | 1.35 | 0.83 |
| 42 | 733 | 860 | 850 | | 1.17 | 1.16 | 1.01 |
| 43 | 916 | 962 | 939 | | 1.05 | 1.03 | 1.02 |
| 44 | 1002 | 906 | 1059 | | 0.90 | 1.06 | 0.86 |
| 45 | 969 | 1034 | 970 | | 1.07 | 1.00 | 1.07 |
| 46 | 756 | 996 | 863 | | 1.32 | 1.14 | 1.15 |
| 47 | 819 | 1049 | 825 | | 1.28 | 1.01 | 1.27 |
| 48 | 700 | 661 | 640 | | 0.94 | 0.91 | 1.03 |
| 49 | 818 | 1008 | 1340 | | 1.23 | 1.64 | 0.75 |
| 50 | 567 | 1004 | 881 | | 1.77 | 1.55 | 1.14 |
| 51 | 871 | 1116 | 1353 | | 1.28 | 1.55 | 0.82 |
| 52 | 520 | 872 | 636 | | 1.68 | 1.22 | 1.37 |
| 53 | 736 | 888 | 1110 | | 1.21 | 1.51 | 0.80 |
| | | | | Average | 1.18 | 1.03 | 1.16 |
| | | | | SD | 0.18 | 0.10 | 0.25 |
| | | | | High Ratio Average | 1.43 | 1.40 | 1.04 |
| | | | | SD | 0.23 | 0.14 | 0.23 |

*FIG. 9*

| Patient ID | Anterior Max | Posterior Max | Tubercle | | P/A ratio | T/A ratio | P/T ratio |
|---|---|---|---|---|---|---|---|
| 54 | 902 | 1341 | 911 | | 1.49 | 1.01 | 1.47 |
| 55 | 894 | 1025 | 955 | | 1.15 | 1.07 | 1.07 |
| 56 | 976 | 1007 | 967 | | 1.03 | 0.99 | 1.04 |
| 57 | 815 | 892 | 709 | | 1.09 | 0.87 | 1.26 |
| 58 | 736 | 1285 | 861 | | 1.75 | 1.17 | 1.49 |
| 59 | 900 | 1120 | 914 | | 1.24 | 1.02 | 1.23 |
| 60 | 830 | 1175 | 919 | | 1.42 | 1.11 | 1.28 |
| 61 | 824 | 1036 | 1087 | | 1.26 | 1.32 | 0.95 |
| 62 | 617 | 1166 | 754 | | 1.89 | 1.22 | 1.55 |
| 63 | 802 | 1110 | 754 | | 1.38 | 0.94 | 1.47 |
| 64 | 838 | 1066 | 917 | | 1.27 | 1.09 | 1.16 |
| 65 | 857 | 1214 | 1071 | | 1.43 | 1.26 | 1.13 |
| | | | | Average | 1.31 | 1.03 | 1.28 |
| | | | | SD | 0.22 | 0.09 | 0.17 |
| | | | High Ratio | Average | 1.52 | 1.27 | 1.21 |
| | | | | SD | 0.33 | 0.05 | 0.30 |

FIG. 10

| Patient ID | Anterior Max | Posterior Max | Tubercle | | P/A ratio | T/A ratio | P/T ratio |
|---|---|---|---|---|---|---|---|
| 66 | 700 | 1078 | 743 | | 1.54 | 1.06 | 1.45 |
| 67 | 1076 | 1100 | 1046 | | 1.02 | 0.97 | 1.05 |
| 68 | 749 | 1278 | 778 | | 1.71 | 1.04 | 1.64 |
| 69 | 729 | 1146 | 928 | | 1.57 | 1.27 | 1.23 |
| 70 | 848 | 919 | 728 | | 1.08 | 0.86 | 1.26 |
| 71 | 766 | 979 | 760 | | 1.28 | 0.99 | 1.29 |
| 72 | 724 | 789 | 895 | | 1.09 | 1.24 | 0.88 |
| 73 | 656 | 830 | 662 | | 1.27 | 1.01 | 1.25 |
| | | | | Average | 1.32 | 0.99 | 1.32 |
| | | | | SD | 0.26 | 0.07 | 0.20 |
| | | | High Ratio | Average | 1.33 | 1.25 | 1.06 |
| | | | | SD | 0.34 | 0.03 | 0.25 |

*FIG. 11*

SYSTEM AND METHOD FOR PREDICTING TISSUE INTEGRITY

CROSS-REFERENCE TO RELATED APPLICATIONS

This application is a divisional of U.S. Pat. No. 10,582,970, filed Jan. 5, 2017, which claims the benefit of the filing date of U.S. Provisional Patent Application No. 62/275,432 filed Jan. 6, 2016, the disclosures of which are hereby incorporated by reference herein.

BACKGROUND OF THE DISCLOSURE

The success of a knee replacement procedure may be dependent at least in part upon the integrity of the anterior cruciate ligament ("ACL") of the patient. For example, unicondylar knee replacement ("UKR") and bi-cruciate retaining knee replacement ("BCR") procedures replace one or more articular surfaces of the knee joint while preserving the ACL. Thus, the constraint provided by the ACL affects the outcome of UKR and BCR procedures, as opposed to knee replacement procedures which sacrifice the ACL.

Physicians may use qualitative tests to determine whether a patient's ACL has ruptured. One such test is an anterior drawer test of the knee. In an anterior drawer test, a patient lies supine with the hips flexed 45° and the injured knee flexed 90°. The physician grasps the lower leg near the knee joint and translates the leg anteriorly. The procedure is performed on both legs, and if the anterior tibial translation of the injured knee is greater than that of the uninjured knee, the physician may diagnose the patient with a ruptured ACL.

Although qualitative ACL integrity tests may provide useful information, such tests are generally binary in that the ACL is diagnosed as intact or ruptured without the ability to reliably diagnose injured but intact ACL conditions. Such tests may also lack reliability. For example, if an anterior drawer test is performed on a patient while the patient's hamstring muscles are contracted, a false negative may result despite the ACL being ruptured. Thus, it would be preferable to have the ability to perform a diagnostic that reliably diagnoses ACL deficiency and is capable of determining the type of deficiency as well as provide quantitative information regarding the integrity of the ACL.

BRIEF SUMMARY

According to one aspect of the disclosure, a method of diagnosing tissue integrity related to a joint of a patient includes imaging a first bone of the joint of the patient and determining a bone density profile of the first bone based on results of the imaging step. The bone density profile of the first bone is compared to at least one reference bone density profile of a reference first bone. The integrity of a tissue with respect to the first bone is predicted based on the comparison. The first bone may be a tibia and the bone density profile of the tibia may include a bone density profile of a sulcus of a medial tibial condyle of the tibia. The reference first bone may be a reference tibia and the at least one reference bone density profile of the reference tibia may include a reference bone density profile of a reference sulcus of a reference medial tibial condyle of the reference tibia. The comparing step may include comparing a location of a first relatively high bone density area of the medial tibial condyle to a location of a second relatively high bone density area of the reference medial tibial condyle. The tissue of the patient may be an anterior cruciate ligament ("ACL") and the predicting step may include predicting the integrity of both an anteromedial bundle of the ACL of the patient and a posterolateral bundle of the ACL of the patient. The predicting step may include identifying a quantitative indicator of a severity of a deficiency of the ACL. The comparing step may be performed autonomously via a computer system. The tissue may have a healthy attachment area with respect to the joint, and predicting the integrity of the tissue may include determining whether a current attachment area with respect to the bone is different than the healthy attachment area.

According to another aspect of the disclosure, a method of diagnosing a knee joint of a patient includes imaging a tibia of the patient, determining a bone density profile of the tibia based on results of the imaging step, inputting information relating to the bone density profile of the tibia into a model, and outputting a predicted integrity of an anterior cruciate ligament ("ACL") of the patient based on the inputting step, wherein the model is formed based on a plurality of reference bone density profiles of a plurality of reference tibias. The bone density profile of the tibia may include a bone density profile of a sulcus of a medial tibial condyle of the tibia. At least one of the plurality of reference bone density profiles of the plurality of reference tibias may include a reference bone density profile of a reference sulcus of a reference medial tibial condyle. The predicting step may include predicting an integrity of both an anteromedial bundle of the ACL of the patient and a posterolateral bundle of the ACL of the patient. The predicting step may include identifying a quantitative indicator of a severity of a deficiency of the ACL. The outputting step may be performed autonomously via a computer system.

According to a further aspect of the disclosure, a method of diagnosing a knee joint of a patient includes imaging a tibia of the patient, determining a bone density profile of the tibia based on results of the imaging step, identifying a first location of a relatively high bone density area of the tibia, determining a second location of a sulcus of a medial tibial condyle of the tibia, determining a distance and orientation of the first location relative to the second location, and predicting an integrity of an anterior cruciate ligament ("ACL") of the patient based on the determined distance and orientation of the first location relative to the second location. The predicting step may include predicting the integrity of both an anteromedial bundle of the ACL of the patient and a posterolateral bundle of the ACL of the patient. The predicting step may include identifying a quantitative indicator of a severity of a deficiency of the ACL. The step of determining a distance and orientation of the first location relative to the second location is performed autonomously via a computer system.

According to yet another aspect of the disclosure, a computer system configured to diagnose a knee joint of a patient may include a memory module adapted to receive at least one medical image of a tibia of the patient. A processor may be configured to analyze the at least one medical image of the tibia of the patient to determine a bone density profile of the tibia. The system may also include a database of reference bone density profiles of reference tibias. The processor may be further configured to compare the bone density profile of the tibia to at least one reference bone density profile in the database and further to predict an integrity of an anterior cruciate ligament ("ACL") of the patient based on the comparison. The bone density profile of the tibia may include a bone density profile of a sulcus of a medial tibial condyle of the tibia. The at least one reference bone density profile of the reference tibia may include a reference bone density profile of a reference sulcus of a reference medial tibial condyle of the reference tibia. The processor may be further configured to compare a location of a first relatively high bone density area of the medial tibial condyle to a location of a second relatively high bone density area of the reference medial tibial condyle. The processor may be further configured to predict an integrity of both an anteromedial bundle of the ACL of the patient and a posterolateral bundle of the ACL of the patient. The processor may be further configured to identify a quantitative indicator of a severity of a deficiency of the ACL.

According to yet a further aspect of the disclosure, a computer system configured to diagnose a knee joint of a patient includes a memory module adapted to receive at least one medical image of a tibia of the patient. A processor may be configured to analyze the at least one medical image of the tibia of the patient to determine a bone density profile of the tibia. The system may also include a computer model adapted to receive an input of information relating to the bone density profile of the tibia and, based on the input information, output a predicted integrity of an anterior cruciate ligament ("ACL") of the patient. The computer model may be formed based on a plurality of reference bone density profiles of a plurality of reference tibias. The bone density profile of the tibia may include a bone density profile of a sulcus of a medial tibial condyle of the tibia. At least one of the plurality of reference bone density profiles of the plurality of reference tibias includes a reference bone density profile of a reference sulcus of a reference medial tibial condyle. The computer model may be configured to predict an integrity of both an anteromedial bundle of the ACL of the patient and a posterolateral bundle of the ACL of the patient. The computer model may be configured to identify a quantitative indicator of a severity of a deficiency of the ACL.

According to still another aspect of the disclosure, a method of diagnosing a knee joint of a patient includes imaging a tibia of the patient at a first time and again at a second time after the first time. A first bone density profile of the tibia is determined based on results of the imaging step at the first time, and a second bone density profile of the tibia is determined based on results of the imaging step at the second time. The second bone density profile is compared to the first bone density profile of the tibia, and a deficiency of an anterior cruciate ligament ("ACL") of the patient is diagnosed based on the comparison.

In all of the above-described methods and systems, the determination of whether an ACL is healthy may be based, at least in part, on whether one or more bone density ratios, for example those described in connection with FIGS. 8-11, of a particular patient are outside the average value expected for a healthy knee of the subgroup of patient (e.g. Caucasian female). Similarly, the determination of the extent of injury to the ACL may be based, at least in part, on the extent of the difference in values of the one or more bone density ratios compared to the average value expected for a healthy knee of the subgroup of patient.

BRIEF DESCRIPTION OF THE DRAWINGS

FIG. 8 is a table of calculated density ratios for Caucasian males expected to have healthy knee joints.

FIG. 9 is a table of calculated density ratios for Caucasian females expected to have healthy knee joints.

FIG. 10 is a table of calculated density ratios for Asian males expected to have healthy knee joints.

FIG. 11 is a table of calculated density ratios for Asian females expected to have healthy knee joints.

DETAILED DESCRIPTION

Body tissues, such as ligaments, tendons, muscles, and fibrocartilage, may affect how one body portion, such as a bone of a joint, interacts with another body portion, such as another bone of the joint. Generally, if a bone or a portion of a bone undergoes frequent loading, the density of the portion of the bone loaded may be generally greater than surrounding bone that undergoes less loading. Although the description below generally pertains to a tissue in the form of the ACL and bones in the form of the knee joint, it should be understood that the concepts disclosed herein may apply with equal force to other tissues and other bones and joints.

Figure 1:
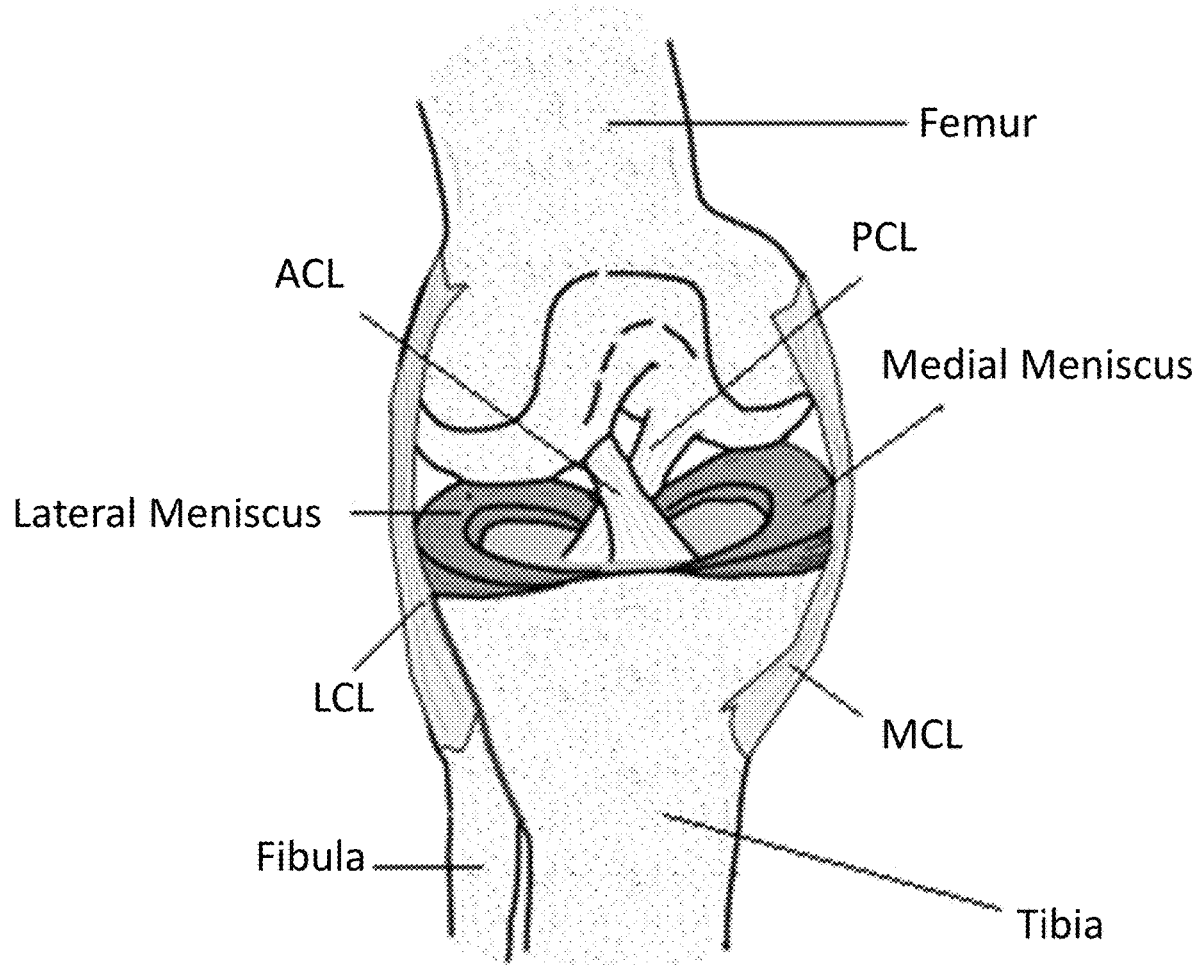
FIG. 1 is a schematic drawing of certain components of a knee joint.

FIG. 1 is a highly simplified illustration of a typical right knee joint of a patient. The medial and lateral condyles of the distal femur articulate with respect to the medial and lateral condyles of the tibia, respectively. The articulation of the femur against the tibia is facilitated by cartilaginous tissue including the medial meniscus, which is attached the medial condyle of the tibia, and the lateral meniscus, which is attached to the lateral condyle of the tibia.

Still referring to FIG. 1, the knee joint is stabilized, in part, by four main ligaments. The ACL connects the femur to the tibia, starting from the posteromedial aspect of the lateral femoral condyle and extending in an anteromedial direction to its point of attachment at the anteromedial aspect of the tibia. The ACL crosses the posterior cruciate ligament ("PCL") and prevents anterior translation and excess rotation of the tibia with respect to the femur. The PCL, on the other hand, connects the posterior intercondylar area of the tibia to the medial condyle of the femur and helps to resist posterior translation of the tibia with respect to the femur. The other major ligaments of the knee include the medial collateral ligament ("MCL") which attaches the medial epicondyle of the femur to the medial condyle of the tibia and resists valgus forces on the knee, and the lateral collateral ligament ("LCL") which attaches the lateral epicondyle of the femur to the head of the fibula and resists varus forces on the knee. The ACL includes two principal fiber bundles, including the anteromedial ("AM") bundle and the posterolateral ("PL") bundle. The AM bundle is tense when the knee is flexed, and helps the knee limit anterior tibial translation when the knee is flexed. The PL bundle is tense when the knee is in extended, and helps the knee limit anterior tibial translation, hyperextension, and rotation.

Figure 2:
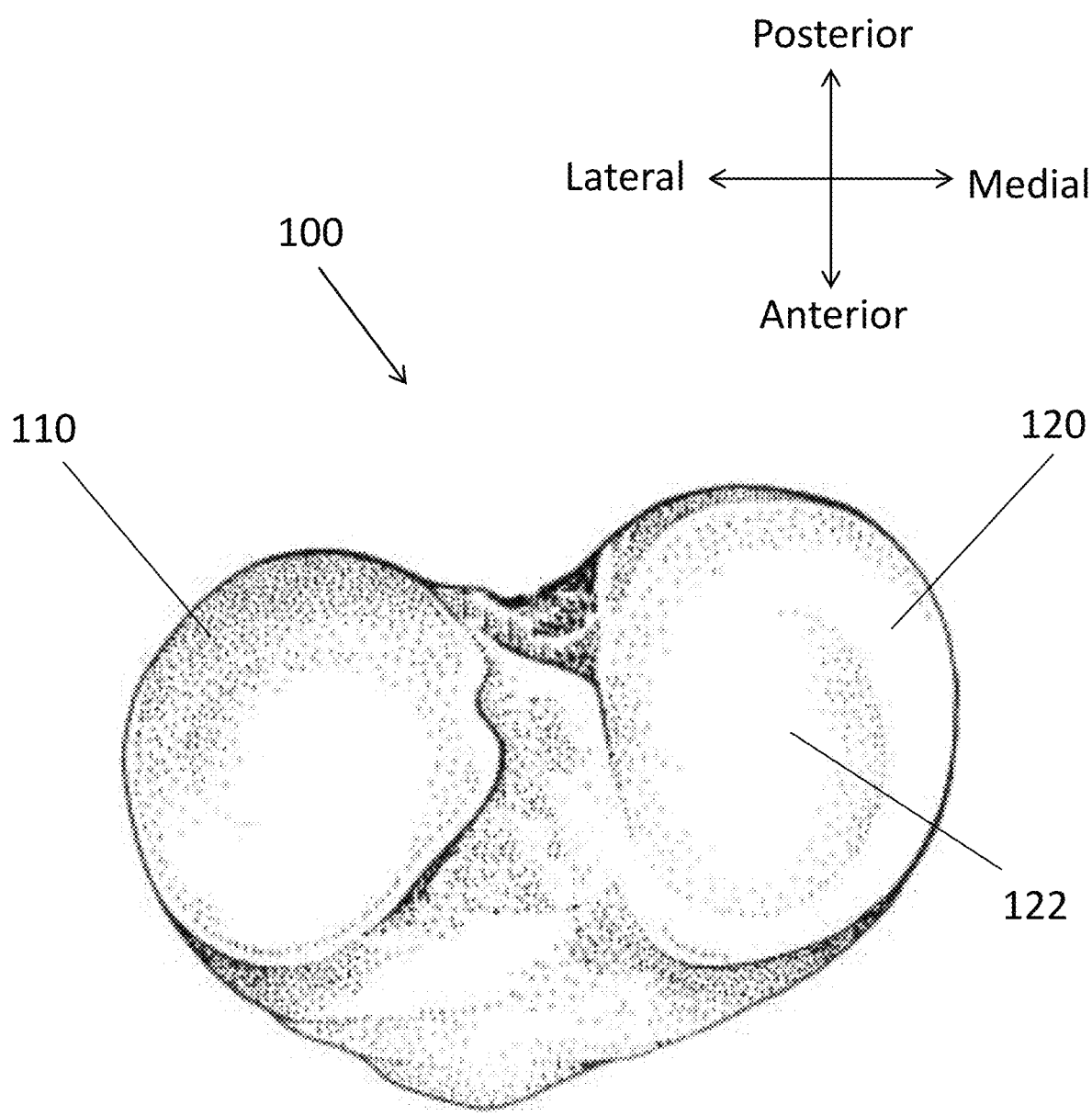
FIG. 2 is a schematic top view of a tibia of a healthy knee.
Figure 3:
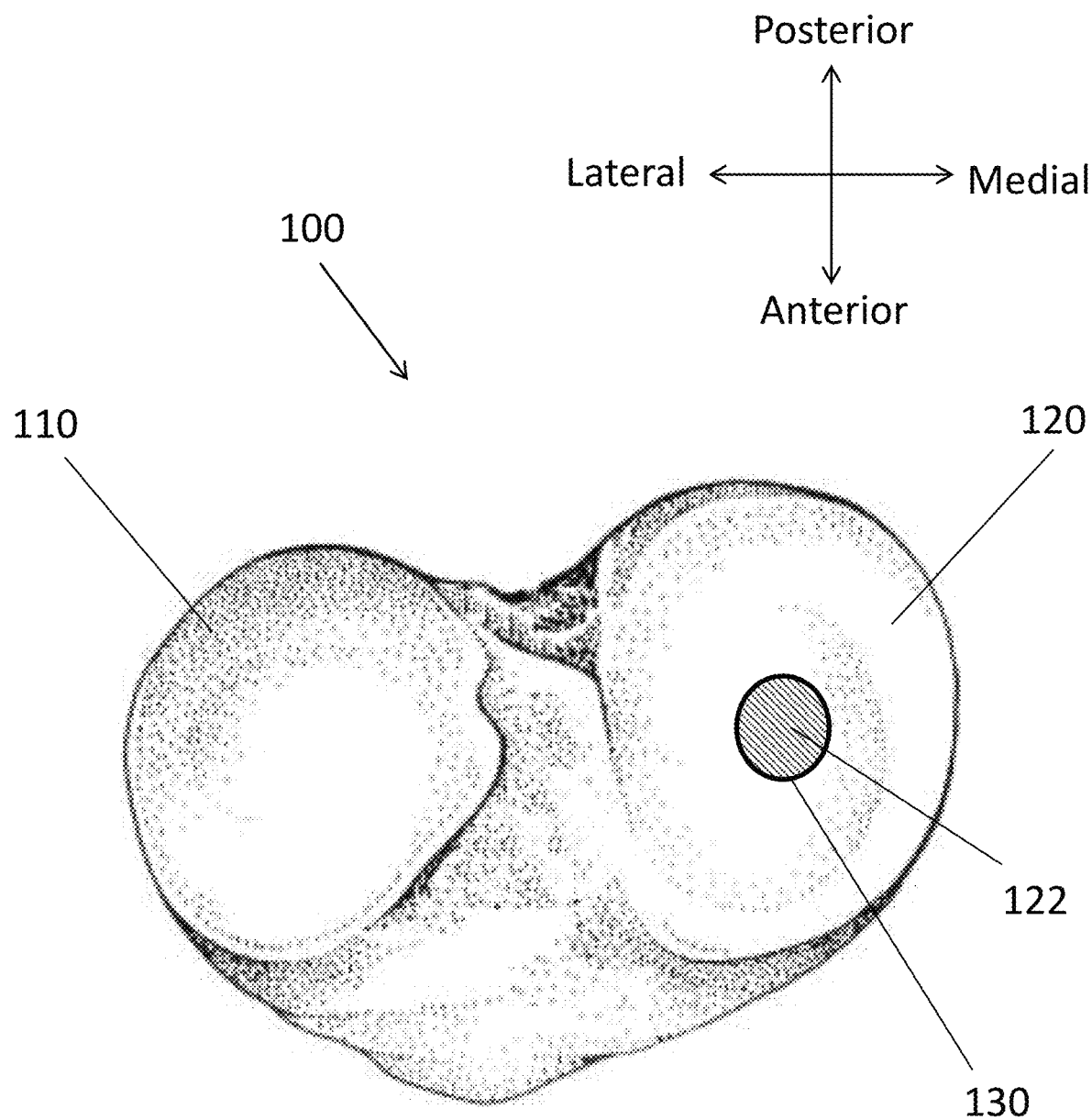
FIG. 3 is a representation of a bone density profile of the medial tibial condyle of the knee of FIG. 2.

A simplified top view of a tibia 100 of a healthy knee is illustrated in FIG. 2. As described above, the medial lateral meniscus sits atop the lateral tibial condyle 110 and the medial meniscus sits atop the lateral tibia condyle 120. During articulation of the femur against the tibia 100, the medial femoral condyle generally makes contact with the medial tibial sulcus 122, which is a concave groove centered on the superior surface of the medial tibial condyle 120. Because bone that experiences greater loading becomes denser than bone that experiences less loading, the density profile of the healthy medial tibial condyle 120 generally includes a relatively high density region 130 at the medial tibial sulcus 122, as shown in FIG. 3.

Figure 4:
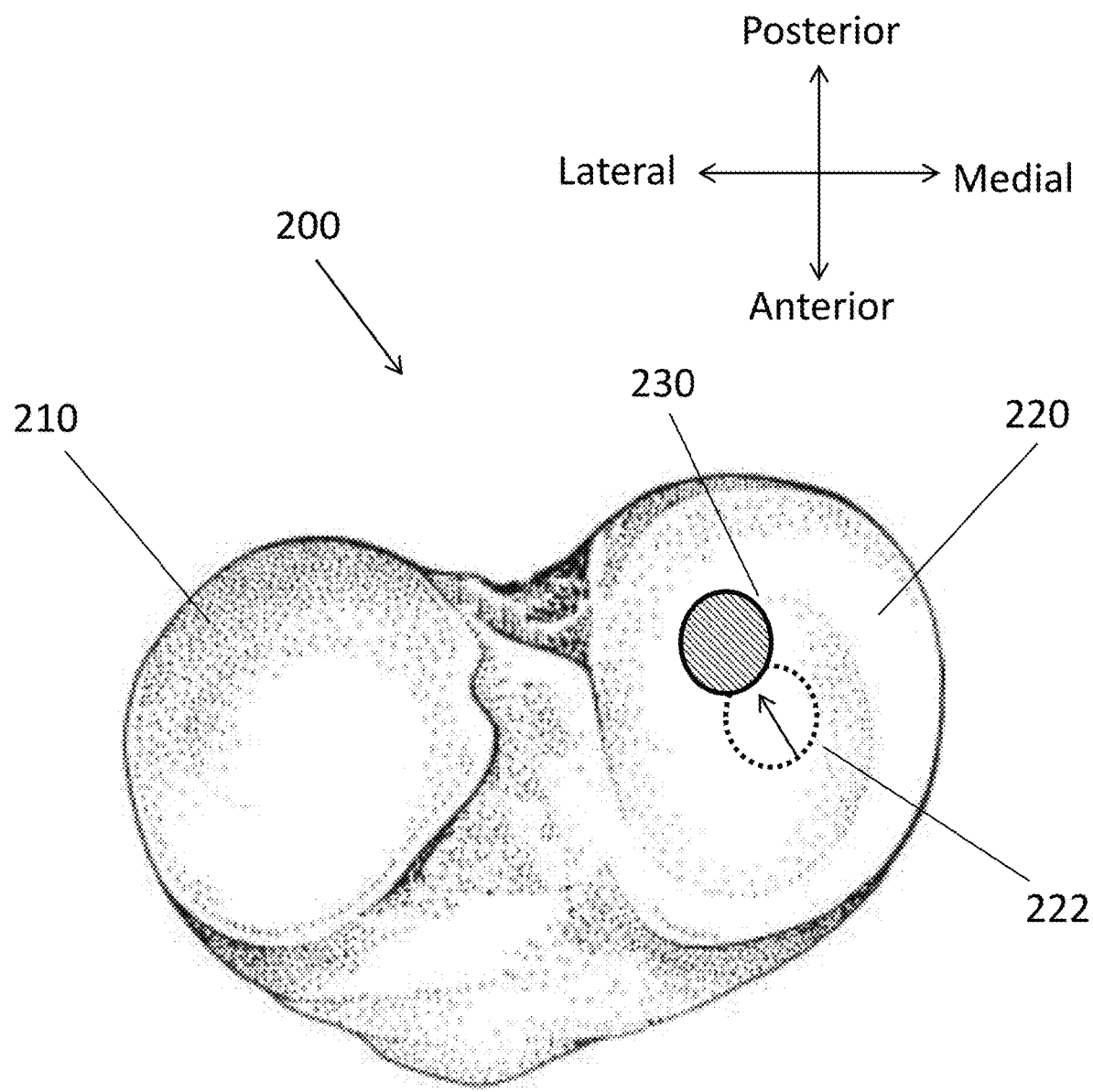
FIG. 4 is a representation of a bone density profile of a medial tibial condyle of a first unhealthy knee.
Figure 5:
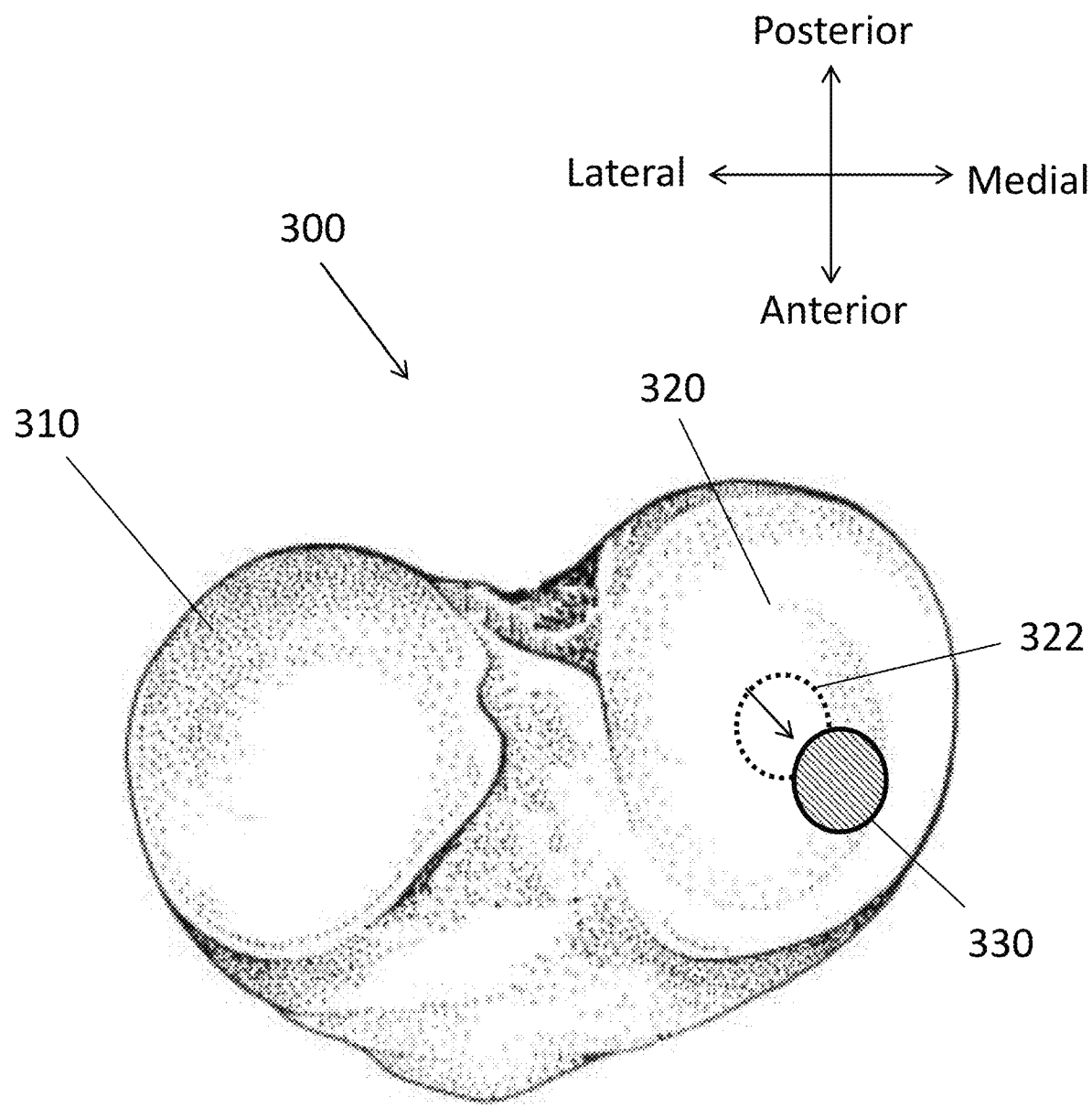
FIG. 5 is a representation of a bone density profile of a medial tibial condyle of a second unhealthy knee.

It has been found that in patients with a deficient ACL, the density profile (or density map) of the medial tibial condyle is non-aligned or shifted relative to what is seen in a healthy patient. For example, a top view of a tibia 200 of an unhealthy knee is illustrated in FIG. 4. The density profiles of one or both of the lateral tibial condyle 210 and medial tibial condyle 220 are different than what is seen in the healthy patient. For example, a deficient ACL may result in a patient's femur loading the tibia 200 at a location posterolateral of the medial tibial sulcus 222. Over time, this shift in loading will cause the bone to remodel and thus the density profile of the medial tibial condyle 220 to correspondingly shift. In particular, when the femur loads the medial tibial condyle 220 in a position posterolateral of the medial tibial sulcus 222, an area of relatively high bone density 230 may be seen in a position posterolateral of the medial tibial sulcus 222. In other words, a longitudinal axis extending through an area of relatively high bone density 230 is offset from a longitudinal axis extending through an area of relatively high bone density 130 shown in FIG. 3. Based upon the shift in loading, the general area of region 130 may not only shift to region 230 but may change in shape such that the area of region 230 is less, more and/or has a perimeter that does not correspond to region 130. Another tibia 300 of an unhealthy knee is shown in FIG. 5. The density profiles of one or both of the lateral tibial condyle 310 and medial tibial condyle 320 are different than what is seen in the healthy patient. However, contrasted to the tibia 200 shown in FIG. 4, the tibia 300 of FIG. 5 shows an area of higher than expected bone density 330 in an anteromedial location compared to the medial tibial sulcus 322. It should be noted that density profiles shown in FIGS. 3-5 are provided in a simplified format for purposes of clarity. In addition, the shifts in bone density profiles are illustrated in an exaggerated format for purposes of clarity. Relatively small shifts in bone density profiles, for example on the millimeter scale, may provide enough information to reliably predict the integrity of the patient's ACL. In addition, although FIG. 4 illustrates a posterolateral shift and FIG. 5 illustrates an anteromedial shift in the relatively high bone density area, it is possible that both shifts may simultaneously occur relative to the sulcus, which may similarly indicate a loss in ACL integrity. Further, although the present disclosure focuses on shifting areas of relatively high bone density in the medial tibial condyle, it should be understood that shifts in relatively high bone density in the lateral tibial condyle may also be analyzed to facilitate diagnosing and/or determining the integrity of the ACL.

Information relating to shifts in bone density profiles of knees, and in particular the medial tibial condyle, may be utilized to non-invasively, accurately, and quantitatively predict the health of the ACL of a patient. This information may be used to inform the decision of what corrective procedure (including which prosthetic components), if any, should be performed on a patient. One example of this process is described in greater detail below in connection with FIGS. 6-7.

Prior to diagnosing a patient, a bone density profile model of the medial tibial condyle may be created. For example, a plurality of individual bone density profiles for patients with known ACL diagnoses may be entered into a database. The database may also include bone density profiles for patients with healthy ACLs. The bone density profiles may consist of images (e.g. x-rays, CT scans, etc.) or any other suitable form of data. The bone density profiles may be grouped by relevant categories including, for example, age group, ethnicity, male/female, and status of ACL (e.g. healthy, deficient AM bundle, deficient PL bundle, deficient AM and PL bundle, completely ruptured ACL, etc.). With enough examples of bone density profiles in the database, a relationship between bone density profiles and the expected ACL deficiency (if any) is created. For example, as shown in FIG. 3, a patient with a bone density profile in which the medial tibial condyle has the greatest density at the medial tibial sulcus 122 may be expected to have an ACL without deficiencies. On the other hand, patients that have the highest density regions of the medial tibial condyle shifted posterolaterally or anteromedially relative to the medial tibial sulcus may be expected to have a deficient ACL, with the type of deficiency being predicted by the particular bone density profile of the patient. In addition to the type of ACL deficiency, a quantitative indicator of the severity of the deficiency, e.g. on a scale of 1-10, may be output based on the bone density profile. The severity of the deficiency may also be quantified so that, depending on the value, a surgical procedure that spares the ACL or, on the other hand, a surgical procedure that sacrifices the ACL is suggested. For example, an ACL with relatively slight injury has the capability of returning to normal function and form if the ACL line of action and tension is restored through surgery using a suitable implant or set of implants as well as proper implant alignment. If the deficiency is so severe that return to normal function is unlikely or impossible, an ACL sacrificing procedure may be indicated by the quantitative indicator. It should be understood that although the bone density profile of a particular patient may be manually (or autonomously) compared to one or more bone density profiles of other patients with known ACL deficiencies, an alternative is to create a statistical (or other) model in which bone density information of a particular patient may be input into the model, the model being based on information derived from the database of bone density profiles of other individuals, and the model may output a diagnosis regarding the expected particular ACL deficiency of the patient. It should further be understood that although CT and other three-dimensional scans may provide for a relatively large amount of information, bone density (and bone density profiles) may be determined based solely on simple x-rays, such as an anterior-posterior ("AP") view x-ray. Using such an x-ray may be particularly desirable because of the relatively low dose of radiation compared to other types of imaging, and the simplicity of obtaining an x-ray of the relevant anatomy in the desired orientation compared to more complex imaging modalities.

Figure 6:
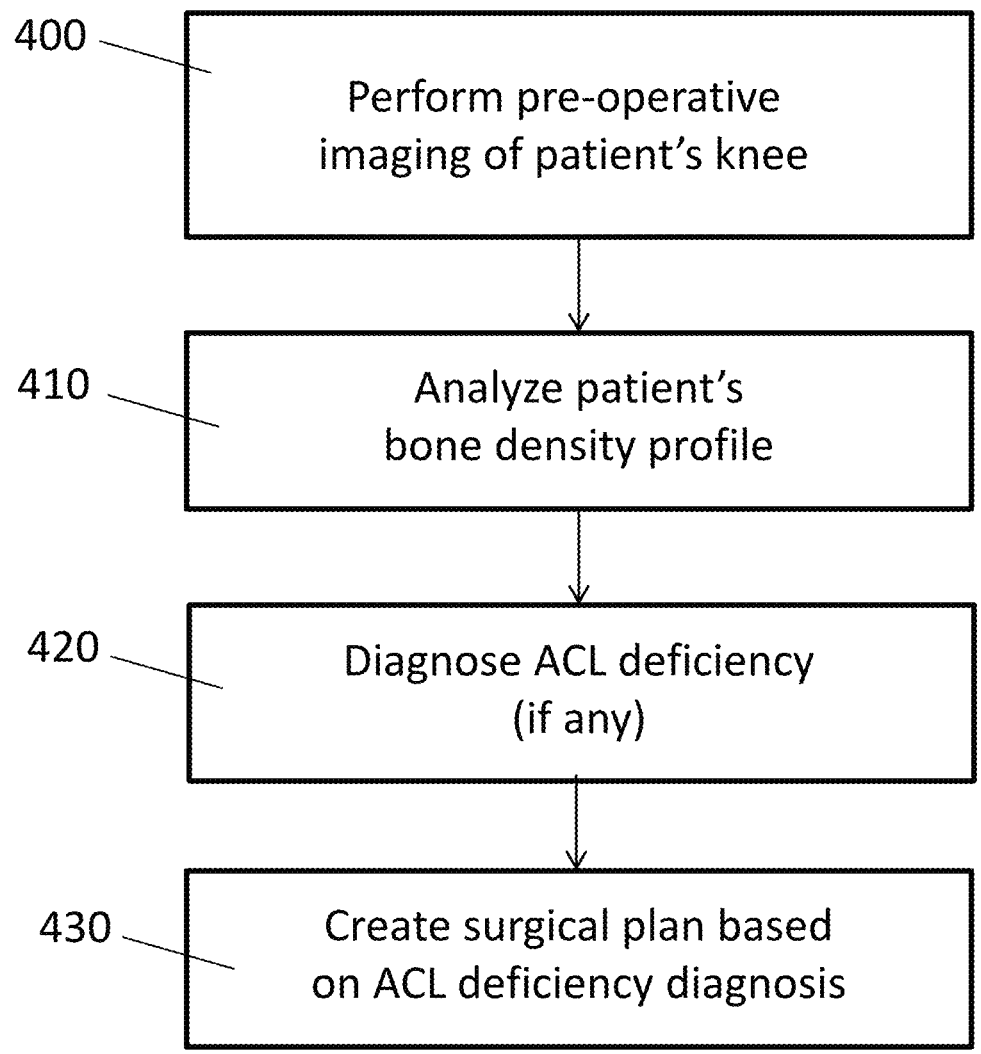
FIG. 6 is a flow chart of a method according to an aspect of the disclosure.
Figure 7:
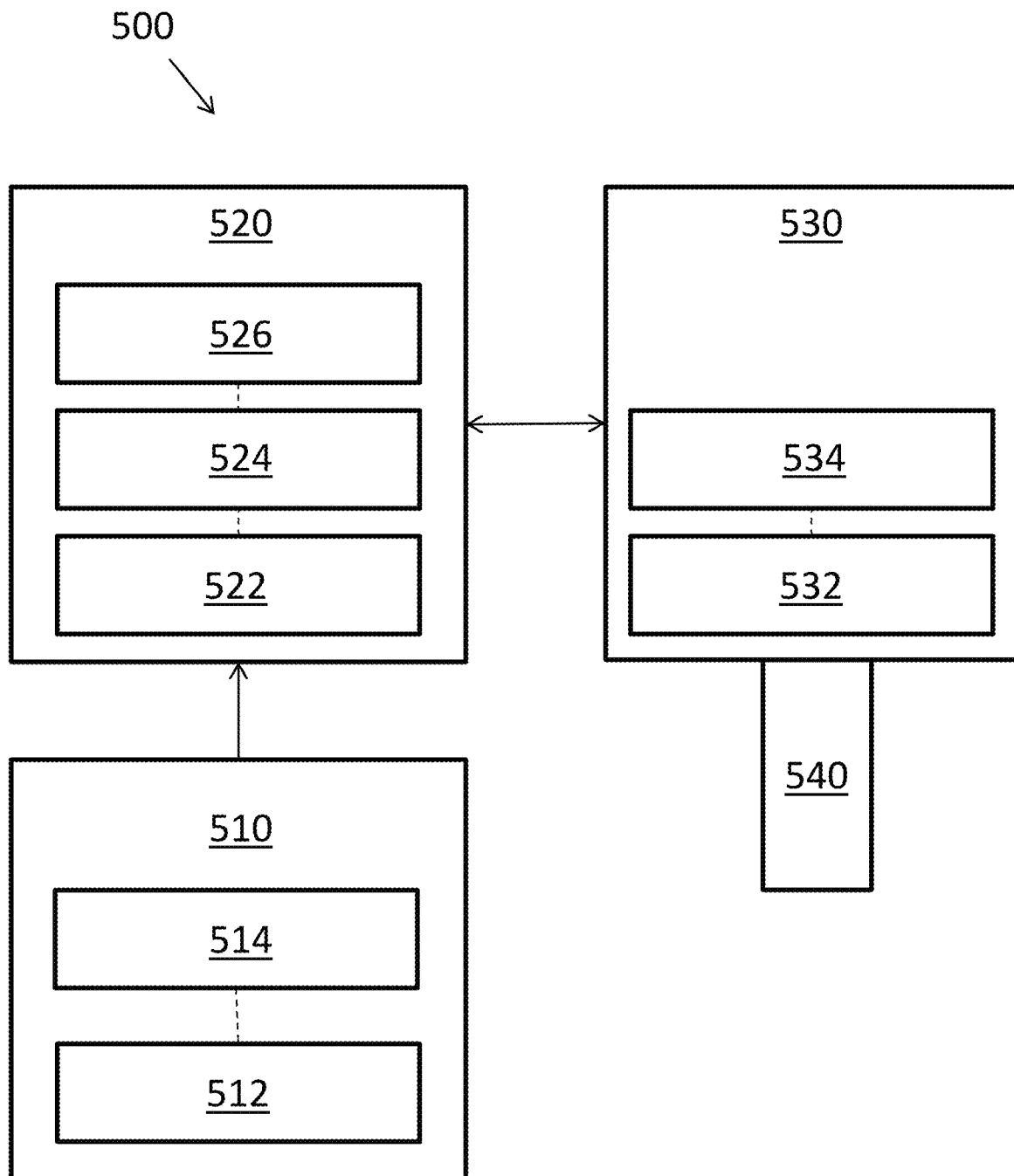
FIG. 7 is a schematic diagram of a system according to an aspect of the disclosure.

One example of a method of predicting ACL integrity and acting on that information, is shown in FIG. 6, with a system of carrying out the method shown in FIG. 7. In a first step 400, one or more pre-operative images of the patient's knee are generated. The imaging may be carried out using any suitable imaging modality, including CT scanning, x-ray imaging, and others. The images of the knee may be stored in memory 512 of a first computer system 510. A processor 514 in computer system 510 may be operatively connected to memory 512 to analyze the bone density profile of the knee images stored in memory 512 in step 410. The bone density analysis may be performed according to known methods, for example by converting Hounsfield Units of a CT image to bone mineral density values. U.S. Patent Publications No. 2015/0119987 and 2015/0080717, which are both hereby incorporated by reference herein, describe methods for mapping bone density. The one or more bone density profiles created may be transferred by any suitable means to a second computer system 520. However, it should be understood that a single computer system may be used or more than two computer systems as desired. It should also be understood that bone density may be analyzed in terms of absolute bone density and/or relative bone density. When determining absolute bone density, a calibration step may be performed with a medical image and/or scan including a bone mineral density phantom or any other suitable means. Relative density, on the other hand, may be analyzed based on, for example, voxel brightness within a CT scan. Relative bone density may be preferable for determining where relatively dense bone is located, but absolute bone density analysis may be necessary to determine the amount of loading on the ACL and to determine if quantitative density of the bone.

In step 420, the ACL deficiency (or lack thereof) of the patient is diagnosed. Computer system 520 may be utilized for the diagnosis. In particular, computer system 520 may include a memory module 522, a bone density profile model and/or database 524, and a processor 526, each of which may be operatively connected to one another. It should be understood that although represented as three modules, memory 522, bone density profile model and/or database 524, and processor 526 may comprise fewer or more modules as desired. The patient's bone density profile previously uploaded to computer system 520 may be compared to information in the bone density profile database 524 in order to diagnose the patient's ACL deficiency. For example, and as noted above, a user may complete this step manually by viewing the patient's bone density profile and comparing to bone density profiles of similar patients (e.g. selected by sex, age, race, etc.) visually on a display device. Preferably, the deficiency diagnosis is a completely or at least partially automated process. When using a bone density profile model 524, for example, information from the patient's bone density profile may be input into the model 524, with the output being a diagnosis of the patient's ACL deficiency, if any exists, which may include a quantitative description of the severity of the deficiency. The diagnosis may alternately be performed autonomously without a statistical model. For example, information relating to the patient's bone density profile may be compared to bone density information of other patients, preferably a relevant subset of patients, stored in database 524 with the aid of processor 526 to determine what deficiency exists in the patient's ACL, if any.

Based on the diagnosis of the patient's ACL integrity from step 420, the surgeon may then create a surgical plan based, at least in part, on the diagnosis in step 430. This step may be performed completely manually or partially or completely autonomously. For example, if a quantitative scale is used, a relatively high score that indicates a relatively high deficiency may indicate a total knee replacement ("TKR") in which the ACL is removed. A relatively low score that indicates a relatively slight deficiency may indicate a BCR implant system or a UKR procedure. A UKR procedure may be appropriate with a healthy (or relatively healthy) ACL, but if the bone density has shifted, fixation of a UKR implant system may be difficult, in which case a BCR implant system may be recommended. A robotic surgical system 530, which may be utilized to carry out the surgical procedure, may include a memory module 532 and a process module 534 operatively connected to one another. The diagnosis from step 420 may be uploaded to robotic surgical system 530 in any suitable manner. The robotic surgical system 530 may suggest a particular procedure to the surgeon, for example via a connected display device, based on the patient's ACL diagnosis. Images and/or 3D models of the patient's knee may be displayed by the robotic surgical system 530, along with models of one or more potential implants, allowing the surgeon to manipulate the models of the implants with respect to the model of the patient's bone to confirm the surgical plan or to otherwise create an alternative surgical plan if the suggested plan is unsatisfactory. Bone density information previously determined may also be displayed by robotic surgical system 530 to provide the surgeon the ability to consider a surgical plan in relation to the patient's bone quality. It should be understood that the computer systems 510, 520, and robotic surgical system 530 need not be provided in the exact formats described above, and the specific example given herein is provided for purposes of clarity. For example, a single computer system may perform all of the image analysis, diagnosis, and surgical planning steps, and the surgical plan ultimately created may be performed by a separate surgical robot operatively connected to the single computer system Once the surgical plan is created (or accepted or otherwise finalized), the surgeon may employ one or more end effectors 540 operable connected to the robotic surgical system 530 to carry out various portions of the surgical procedure, for example including resurfacing the proximal tibia and/or distal femur to prepare the bone to accept one or more prosthesis, and actual placement of the prosthetic components in a desired position and/or orientation. One such robotic surgical system 530 that may be utilized is described in greater detail in U.S. Pat. No. 8,095,200, the disclosure of which is hereby incorporated by reference herein.

The disclosure provided herein may provide additional avenues for diagnosing and determining the integrity of a patient's tissue such as the ACL. For example, medical personnel may create medical images of a patient at periodic intervals over time, including at times before any tissue injury is suspected. For example, a patient may have a knee joint imaged via any suitable imaging modality every year, every other year, every five years, etc. The medical image or images created when the patient is presumed to have a healthy ACL may be used to track bone density profiles of the specific patient over time. In other words, the earlier images provide bone density profile information to be used as a baseline. The bone density profile over time information for a specific patient may provide a number of benefits. First, a shift of bone density from baseline may be more clearly recognizable since baseline information of the healthy patient is available. Second, such a shift in bone density profile may be recognized relatively early, which may allow intervention at a time when the ACL is still capable of being preserved. Third, the baseline information may provide information a target so that a surgical intervention may be planned with the goal of modifying the patient's joint anatomy to return the joint to the earlier state which resulted in the baseline bone density profile. Fourth, a patient's baseline density profile may be used to track progress and recovery back to the expected loading norm following intervention (such as prosthesis implantation) for purposes of, for example, tracking clinical outcomes.

Still further, densities, and particular density ratios, of certain anatomical landmarks of a tibia may be analyzed to further assist in the determination of the health of the ACL. The inventors analyzed a plurality of medical images of knees of Caucasian males (FIG. 8), Caucasian females (FIG.

9), Asian males (FIG. 10), and Asian females (FIG. 11). Each patient was selected from the Stryker Orthopaedics Modeling and Analytics system ("SOMA") database. In particular, each patient was selected based on patient characteristics that would be expected to correspond to a healthy knee, such as age and body mass index ("BMI"). The individual patients, who have been given arbitrary patient identifiers in FIGS. 8-11, were controlled for height (between 140-199 cm), weight (between 40-100 kg), age (21-55 years), body mass index ("BMI") (<30), sex (male or female), and race (Caucasian or Asian). Each patient's medical image was analyzed to determine maximum densities at the anterior tibia, the posterior tibia, and the tibial tubercle. The units provided in FIGS. 8-11 are Hounsfield value units, which generally correspond to bone density. However, due to scaling differences, ratios of Hounsfield values were calculated to normalize the data. In particular, as shown in FIGS. 8-11, the ratios calculated include: (1) the maximum posterior tibial density to the maximum anterior tibial density ("P/A ratio"); (2) the maximum tibial tubercle density to the maximum anterior tibial density ("T/A ratio"); and (3) the maximum posterior tibial density to the maximum tibial tubercle density ("P/T ratio"). These point clusters were selected from the locations known to be the anatomical attachment sites of the ACL, PCL, and the patellar tendon. Patients in FIGS. 8-11 with particularly high density ratios are shown with a stippled background, and the average density ratio and standard deviations were calculated for those patients separately in a "High Ratio" group.

As can be seen from the data presented in FIGS. 8-11, the standard deviations ("SD") for each density ratio for the group of Caucasian males (FIG. 8), the group of Caucasian females (FIG. 9), the group of Asian males (FIG. 10), and the group of Asian females (FIG. 11) is small. In other words, a male Caucasian individual with a healthy knee would be expected to have a P/A ratio of near 1.53, a T/A ratio of near 1.02, and a P/T ratio of near 1.49. A female Caucasian individual with a healthy knee would be expected to have a P/A ratio of near 1.18, a T/A ratio of near 1.03, and a P/T ratio of near 1.16. A male Asian individual with a healthy knee would be expected to have a P/A ratio of near 1.31, a T/A ratio of near 1.03, and a P/T ratio of near 1.28. A female Asian individual with a healthy knee would be expected to have a P/A ratio of near 1.32, a T/A ratio of near 0.99, and a P/T ratio of near 1.32. Even across the male and female and Caucasian and Asian data, a T/A ratio of near 1 (or slightly above 1) appears to be expected for an individual with a healthy knee, whereas a significant deviation from a T/A ratio of about 1 may indicate the ACL or other anatomy of the knee is injured or is otherwise unhealthy. It should be understood that the values provided in FIGS. 8-11 are exemplary, and different sub-groups of individuals may be expected to have different density ratios for healthy knee joints depending on the particular population of interest.

The data provided in FIGS. 8-11 may provide for an objective and relatively simple analysis of a patient's medical image (such as an X-ray, including a single AP X-ray, or CT scan or scan slice) to determine whether the maximum density ratios of the posterior tibia, the anterior tibia, and the tibial tubercle are within an expected healthy range for a given population set. In some embodiments, a maximum density ratio of any or all of the P/A ratio, T/A ratio, and P/T ratio outside the expected value may be indicative of an unhealthy knee. In other embodiments, the extent that the maximum density ratio of any or all of the P/A ratio, T/A ratio, and P/T ratio falls outside the expected range may provide an extent of the likely problem. For example, if a male Caucasian patient has a T/A ratio that varies from the 1.02 average value in FIG. 8, a physician may have a basis to determine that there may be a problem with the knee joint, with the extent of deviation from the 1.02 average indicating the extent of the problem, such as the type and severity of ACL impairment. It may also be possible to determine the type of impairment of the ACL based on which of the ratios deviate from an expected value, and by how much the ratios deviate from that expected value.

Referring back to FIGS. 3-5, it should be understood that additional information may be obtained from tibial bone density maps that may assist in diagnosing a condition. For example, females who are prone to hyperextending the knee generally encounter more anterior and medial loading of the femur onto the tibia, which may correspond to greater bone density in these areas. On the other hand, males who are prone to hyperextending the knee generally see additional loading only in the medial direction of the tibia. Thus, this information may be used to help explain deviations in a tibial bone density map and thus assist in diagnosing the condition of the knee joint.

Still further, medical images such as X-rays or CT scans may be used similar to the manner described above to help predict certain soft tissue deformities that relate to knee joint kinematics. For example, a number of foot types may correspond to knee joint kinematics, including high arch, talipes cavus, cavoid foot, and supinated foot type (e.g. instepper or outstepper). The tibia of an individual that is an instepper (which may correspond to a flat-footed patient) may be rotated internally when bearing the weight of the femur during a gait, which may result in a tibial bone density map that deviates from an individual that is neither an instepper nor an outstepper. On the other hand, an individual that is an outstepper (which may correspond to a high-arched patient), may similarly see a different variation in the tibial bone density map. Although these conditions may result in a change in tibial bone density profile, such conditions may not necessarily indicate a problem with the ACL (or other components of the knee joint). Thus, in addition to determining variations in bone density profile of a patient's tibia, information relating to a patient's foot type or reported step conditions may be used, at least in part, in a holistic analysis of variations in a patient's tibial bone density profile to determine the likelihood and type of injuries or pathologies to the patient's knee joint.

Still further, the change in the tibial bone density profile over time may provide valuable information for patients having undergone either a TKA or UKA. In other words, if a patient receives a knee implant, the tibial bone density profile may be mapped over time to determine what changes are occurring as a result of changes in knee kinematics after the implant procedure. If the tibial bone density profile shifts over time to a density profile that would be expected for a similar patient with a healthy knee joint, such a change may help confirm that the knee implant is functioning desirably. However, if the bone density profile is not shifting toward what would be expected of a similar patient with a healthy knee joint, or is even shifting farther away from what would be expected of a similar patient with a healthy knee joint, such changes may be indicative of a problem with the knee implant. This type of analysis may be especially useful for a patient that has undergone a UKA procedure. For example, in patients undergoing UKA procedures, the previously healthy tibial condyle may undergo bone density profile changes as a result of the implant that replaced the unhealthy condyle. In such situations, it may be determined that the UKA implant is either not performing satisfactorily and/or that the disease is moving to the previously healthy condyle, which situations may indicate a need for a replacement of the previously healthy tibial condyle. Still further, useful information may be determined from monitoring the changes in tibial bone density profile of a patient that has undergone an ACL-sparing knee replacement and has received a BCR implant. As noted above, a BCR implant may be used for a patient that has a suitably functioning ACL. Changes in tibial bone density after a BCR implant procedure may indicate, for example, that the ACL is not being properly engaged, or is otherwise not loading as would be seen in a healthy patient's ACL. In such situations, it may be determined that the ACL is being rendered mostly useless and there was no advantage in using a BCR as opposed to an ACL-sacrificing knee implant. This information may assist a physician or other medical personnel in determining what the next course of treatment—if any—should be.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of diagnosing tissue integrity related to a joint of a patient, the method comprising:
   imaging a first bone of the joint of the patient;
   determining a bone density profile of the first bone based on results of the imaging step;
   comparing the bone density profile of the first bone to at least one reference bone density profile of a reference first bone; and
   predicting an integrity of a tissue with respect to the first bone based on the comparison,
   wherein the tissue of the patient is an anterior cruciate ligament ("ACL") and the predicting step includes identifying a quantitative indicator of a severity of a deficiency of the ACL.

2. The method of claim 1, wherein the first bone is a tibia and the bone density profile of the tibia includes a bone density profile of a sulcus of a medial tibial condyle of the tibia.

3. The method of claim 2, wherein the reference first bone is a reference tibia and the at least one reference bone density profile of the reference tibia includes a reference bone density profile of a reference sulcus of a reference medial tibial condyle of the reference tibia.

4. The method of claim 3, wherein the comparing step includes comparing a location of a first relatively high bone density area of the medial tibial condyle to a location of a second relatively high bone density area of the reference medial tibial condyle.

5. A method of diagnosing tissue integrity related to a joint of a patient, the method comprising:
   imaging a first bone of the joint of the patient;
   determining a bone density profile of the first bone based on results of the imaging step;
   comparing the bone density profile of the first bone to at least one reference bone density profile of a reference first bone; and
predicting an integrity of a tissue with respect to the first bone based on the comparison,
   wherein the tissue of the patient is an anterior cruciate ligament ("ACL") and the predicting step includes predicting an integrity of both an anteromedial bundle of the ACL of the patient and a posterolateral bundle of the ACL of the patient.

6. The method of claim 1, wherein the comparing step is performed autonomously via a computer system.

7. A method of diagnosing tissue integrity related to a joint of a patient, the method comprising:
   imaging a first bone of the joint of the patient;
   determining a bone density profile of the first bone based on results of the imaging step;
   comparing the bone density profile of the first bone to at least one reference bone density profile of a reference first bone; and
   predicting an integrity of a tissue with respect to the first bone based on the comparison,
   wherein the tissue has a healthy attachment area with respect to the joint, and wherein predicting the integrity of the tissue includes determining whether a current attachment area with respect to the bone is different than the healthy attachment area.

8. The method of claim 1, wherein imaging the first bone of the joint of the patient includes performing X-ray imaging or CT-imaging.

9. The method of claim 1, further comprising inputting information relating to the bone density profile of the first bone into a model.

10. The method of claim 9, wherein the model is formed based on a plurality of reference bone density profiles of a plurality of reference first bones.

11. The method of claim 10, wherein predicting the integrity of the tissue with respect to the first bone based on the comparison includes outputting the predicted integrity of the tissue based on the inputting step.

12. The method of claim 11, wherein the outputting step is performed autonomously via a computer system.

* * * * *